United States Patent [19]

Vlodavsky et al.

[11] Patent Number: 4,882,318

[45] Date of Patent: Nov. 21, 1989

[54] METHOD FOR DECREASING TUMOR METASTASIS

[75] Inventors: Israel Vlodavsky; Amiram Eldor; Yaakov Naparstek, all of Jerusalem; Irun R. Cohen, Reheovot, all of Israel

[73] Assignees: Hadassa Medical Organization, Jerusalem; Yeda Research and Development Company Limited, Rehovot, both of Israel

[21] Appl. No.: 67,582

[22] Filed: Jun. 24, 1987

[30] Foreign Application Priority Data

Jun. 26, 1986 [IL] Israel ............................................. 79255

[51] Int. Cl.$^4$ ..................... A61K 31/725; C08B 37/10
[52] U.S. Cl. ........................................... 514/56; 536/21
[58] Field of Search ............................. 514/56; 536/21; 435/184, 232

[56] References Cited

U.S. PATENT DOCUMENTS 3,033,750  5/1962  Velluz et al. ........................... 536/21
4,575,056  7/1988  Van Gorp et al. ..................... 514/54

FOREIGN PATENT DOCUMENTS 114589  8/1984  European Pat. Off. .............. 514/56

OTHER PUBLICATIONS

Folkman et al, Science, vol. 221, 19 Aug. 1983, pp. 719–725.

*Primary Examiner*—Jacqueline M. Stone
*Attorney, Agent, or Firm*—Browdy and Neimark

[57] ABSTRACT

The invention relates to pharmaceutical compositions intended to decrease the incidence of tumor metastasis in patients who suffer from malignant diseases.

The pharmaceutical compositions of the invention contain as active ingredient heparin or a suitable derivative thereof. Amongst suitable derivatives are N-desulfated and N-acetylated heparin.

The dosage of the administered heparin or heparin derivative is quite critical and will generally be in the range of from 0.05 mg/kg/day to about 0.5 mg/kg/day. A preferred range is between about 0.1 mg/kg/day to about 0.5 mg/kg/day.

3 Claims, No Drawings

METHOD FOR DECREASING TUMOR METASTASIS

FIELD OF THE INVENTION

The invention relates to medications for use in the therapy of malignant diseases. More specifically, it relates to means adapted to decrease the incidence of tumor metastasis. The pharmaceutical compositions comprise an effective dosage of heparin, which is quite critical, or of an effective derivative thereof.

BACKGROUND OF THE INVENTION

The process of metastasis, the dissemination of tumor cells to sites in the body distant from the original site of the tumor, often involves invasion of blood vessels by the tumor cells. The blood vessel wall includes a dense extracellular matrix (ECM) of connective tissue that must be penetrated by any cell entering or leaving the vessel. The ECM includes a proteoglycan scaffold that constitutes a physical barrier to cell penetration.

It was found by the research groups of Vlodavsky (Vlodavsky, J. Fuks, Z. and Schirrmacher, V. In: The Endothelial Cell—A Pluripotent Cell of the Vessel Wall. Eds. Thilo-Korner, D.G.S. and Fresney, R.I., Basel: Karger, pp. 126-157, 1983; Vlodavsky, I., Fuks, Z., Bar-Ner, M, and Schirrmacher, V. Cancer Res. 43: 2704, 1983) and of Nicolson (Nakajima, M. Irimura, T., DiFerrante, D., Ferrante, N. and Nicolson, G.L. Science 220: 611, 1983) that tumor cells that were highly metastatic expressed an enzyme, heparanase, that attacked the heparan sulfate moiety of the ECM proteoglycans. Tumor cells that were less metastatic expressed less heparanase enzyme. Heparanase activity was also associated with the capacity of non-tumor cells such as T lymphocytes to move through blood vessels.

In view of the above, we have considered the possibility that inhibitors of heparanse enzyme activity might handicap the movements of cells into and out of blood vessels, thereby obstructing the metastasis of tumor cells leading to prolongation of life. Experiments in this direction have confirmed that positive results can be obtained, as set out in the following.

SUMMARY OF THE INVENTION

According to the invention there are provided pharmaceutical compositions adapted to decrease metastasis dissemination in mammals, including humans. The compositions contain a predetermined quantity of the effective agent, which dosage is quite critical. The active ingredient is heparin or an effective derivative thereof, such as N-desulfated, N-acetylated heparin. The dosage is in the range of about 0.05 mg/kg/day to about 0.5 mg/kg/day of the active ingredient, preferably about 0.1 mg/kg/day to about 0.3 mg/kg/day.

1. Table 1 shows the effect of the administration of heparins on the ability of heparanase to degrade the heparan sulfate in ECM. It can be seen that intact heparin and N-desulfated, N-acetylated heparin, but not totally desulfated heparin, are active as inhibitors of heparanse activity.

2. Inhibition of Tumor Metastasis by Heparins

Table 2 shows the results of treating mice with heparins on metastasis of 3LL Lewis lung carcinoma cells. C57BL/6 mice were implanted in a hind footpad with 3LL tumor cells and the local tumor was amputated when it reached a size of 8 mm. Two weeks later the number of lung metastases were counted. It can be seen that total desulfated heparin failed to reduce the number of lung metastases. However, treatment with 5 $\mu$g of intact heparin or N-desulfated, N-acetylated heparin, reduced by about one half the number of lung metastases. A higher dose of N-desulfated, N-acetylated heparin (50 $\mu$g) did not give better results, and actually seemed to allow formation of a greater number of metastases. Thus, a dose of about 5 $\mu$g/mouse (0.25 mg/kg) was optimal in preventing metastasis. This indicates that the dosage of heparin is very important.

3. Modified Heparin Treatment prolongs Survival of Mice challenged with EL-4 Tumor Cells Table 3 shows that treatment of mice with N-desulfated, N-acetylated heparin, prolongs life from 16 to 19 days (highly significant by the Wilcoxin Rank Order Test). EL4 injected intraperitoneally is thought to kill mice by metastasizing. Therefore, heparin treatment can prolong life, probably by means of reduction of metastasis (Table 2).

4. Reduction of Metastasis of Melanoma Cells by Administration of Heparin

C57BL/6 mice were inoculated intravenously with $5 \times 10^4$ B16 melanoma cells and 18 days later the mice were killed and their lungs examined for the number of metastases. The results in Table 2 indicate that heparin treatment markedly reduced the numbers of lung metastases. Therefore, similar to the 3LL and EL4 tumors, the B16 melanoma is susceptible to treatment.

CONCLUSIONS

1. Low dose heparin treatment of humans causes a decrease in DTH reactions. This was shown in the animal studies to be due to inhibition of heparanase and T lymphocyte migration to the site of antigen.

2. Treatment of diseases such as rheumatoid arthritis appear to be effective.

TABLE 1

| Heparins inhibit heparanase activity | |
|---|---|
| Inhibitor (1 $\mu$g/ml) | Inhibition of heparanase activity |
| None | No |
| Heparin | Yes |
| Heparin: N—desulfated, N—acetylated | Yes |
| Heparin: Total Desulfated | No |

Heparanase activity was tested in the presence of heparins at a concentration of 1 $\mu$g/ml as described by Vlodavsky, I. et al. In: Extracellular Matrix: Structure and Function 283-308, 1985). N-desulfated, N-acetylated heparin and totally desulfated heparin was prepared as described (Ayotte, L. and Perlin, A.S. Carbohydrate Res. 145: 267, 1986). Inhibition of heparanase activity was detected by failure to obtain $^{35}$S-labeled heparan sulfate degradation products.

TABLE 2

| Inhibition of 3LL lung metastases by heparin and modified heparin | | | |
|---|---|---|---|
| Treatment | $\mu$g | No. of metastases | Median |
| Saline | — | TMTC,TMTC,17,15,5 | 17 |
| Heparin: Total desulfated | 5 | TMTC,20,19,15,14 | 19 |
| Heparin: N—desulfated, N—acetylated | 5 | 10,9,8,6,4 | 8 |
|  | 50 | 6,9,10,15,17 | 10 |

TABLE 2-continued

| Inhibition of 3LL lung metastases by heparin and modified heparin | | | |
|---|---|---|---|
| Treatment | μg | No. of metastases | Median |
| Heparin | 5 | 14,10,9,6,4 | 9 |

C57BL/6 female mice, 2 months old, received $3 \times 10^5$ 3LL (Lewis lung carcinoma) cells in a hind foot pad. When the tumor reached a diameter of 8 mm, the foot was amputated painlessly above the knee and 14 days later the mice were sacrificed and the lungs examined for the number of metastases. Groups of mice were treated from the beginning of the experiment of subcutaneous injections of saline (control) or heparin (Leo, Denmark) N-desulfated, N-acetylated or total desulfated heparins prepared as described (Ayotte, L. and Perlin, A.S. Carbohydrate Res. 145: 267, 1986). TMTC=too many to count.

TABLE 3

| Prolongation of survival of mice injected with EL4 tumor cells by treatment with modified heparin. | | |
|---|---|---|
| Treatment | EL4 tumor Day of death | Median |
| Saline | 16,16,16,16,16 | 16 |
| Heparin: N—desulfated, N—acetylated | 17,18,18,18,19,19,19,19,20 | 19 |

C57BL/6 female mice, 7 months old, were inoculated intraperitoneally with $10^4$ EL4 tumor cells. One day earlier and daily until death, the mice received subcutaneous injections of 5 ug of heparin: N-desulfated, N-acetylated. The day of death from lung metastases was recorded.

TABLE 4

| Reduction of lung metastases of B16 melanoma cells. | | |
|---|---|---|
| No of mice | Heparin (u.g daily) | No. of lung metastases |
| Experiment 1. | | |
| 4 | 0 | 30 ± 8.5 |
| 5 | 5 | 14.7 ± 4.9 |
| 5 | 20 | 16.6 ± 4.8 |
| 5 | 50 | 18.8 ± 3.5 |
| Experiment 2. | | |
| 9 | 0 | 4.4 ± 0.4 |
| 9 | 20 | 1.1 ± 0.1 |
| 7 | 100 | 0.7 ± 0.1 |

Similar results were obtained with equivalent doses of N-desulfated, N-acetylated heparin.

We claim:

1. A method for decreasing tumor metastasis in a mammal comprising the step of administering intact heparin or N-desulfated, N-deacetylated heparin at a dosage of about 0.05 mg/kg/day–0.5 mg/kg/day to a mammal having a malignant tumor.

2. The method of claim 1, wherein said dosage is about 0.1–0.5 mg/kg/day.

3. The method of claim 1, wherein said dosage is about 0.1–0.3 mg/kg/day.

* * * * *

UNITED STATES PATENT AND TRADEMARK OFFICE
CERTIFICATE OF CORRECTION

PATENT NO. : 4,882,318
DATED : November 21, 1989
INVENTOR(S) : VLODAVSKY et al.

It is certified that error appears in the above-identified patent and that said Letters Patent is hereby corrected as shown below:

Title page:

[75] Inventors: line 3      Delete "Reheovot", insert therefor -- Rehovot --

[57] ABSTRACT, lined 6 & 7      Delete "N-desulfated and N-acetylated", insert therefor -- N-desulfated, N-acetylated --

Column 1, lines 38 & 61      Delete "heparanse", insert therefor -- heparase --

Claim 1, Column 4, line 24      Delete "N-deacetylated", insert therefor -- N-acetylated --

Signed and Sealed this

Fourth Day of February, 1992

Attest:

HARRY F. MANBECK, JR.

Attesting Officer      Commissioner of Patents and Trademarks